(12) United States Patent
Michelson

(10) Patent No.: US 6,537,279 B1
(45) Date of Patent: *Mar. 25, 2003

(54) DEVICE AND METHOD FOR PREPARING A SPACE BETWEEN ADJACENT VERTEBRAE TO RECEIVE AN INSERT

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 235 days.

This patent is subject to a terminal disclaimer.

(21) Appl. No.: 09/608,955

(22) Filed: Jun. 30, 2000

Related U.S. Application Data

(63) Continuation of application No. 09/094,036, filed on Jun. 9, 1998, now Pat. No. 6,083,228.

(51) Int. Cl.⁷ .............................................. A61B 17/00
(52) U.S. Cl. ................................................... 606/79
(58) Field of Search .......................... 606/79, 80, 81, 606/82, 85, 167, 169, 168, 170, 171, 180; 15/22.1, 22.2, 22.4

(56) References Cited

U.S. PATENT DOCUMENTS

| | | |
|---|---|---|
| 3,937,222 A | 2/1976 | Banko |
| 4,842,578 A | 6/1989 | Johnson et al. |
| 5,189,751 A | 3/1993 | Giuliani et al. |
| 5,263,218 A | 11/1993 | Giuliani et al. |
| 5,305,492 A | 4/1994 | Giuliani et al. |
| 5,378,153 A | 1/1995 | Giuliani et al. |
| 5,383,242 A | 1/1995 | Bigler et al. |
| 5,387,215 A | 2/1995 | Fisher |
| 5,435,034 A | 7/1995 | Bigler et al. |
| 5,465,444 A | 11/1995 | Bigler et al. |
| 5,601,556 A | 2/1997 | Pisharodi |
| 5,853,415 A | 12/1998 | Bertin et al. |
| 5,904,687 A | 5/1999 | Del Rio et al. |
| 6,083,228 A | * 7/2000 | Michelson ............... 606/79 |

* cited by examiner

Primary Examiner—John J. Wilson
Assistant Examiner—Robyn Kieu Doan
(74) Attorney, Agent, or Firm—Martin & Ferraro, LLP

(57) ABSTRACT

A device and method for use in a human spine to prepare a space between adjacent vertebral bodies and into the vertebral end plates to receive an implantable insert. The device includes a handle, a shaft, and a mounting member at one end of the shaft. An abrading element is mounted on the mounting member and is coupled to a drive mechanism. The drive mechanism is operable to move the abrading element in at least one degree of freedom to create surfaces having predetermined contours in the end plates of the adjacent vertebral bodies.

30 Claims, 8 Drawing Sheets

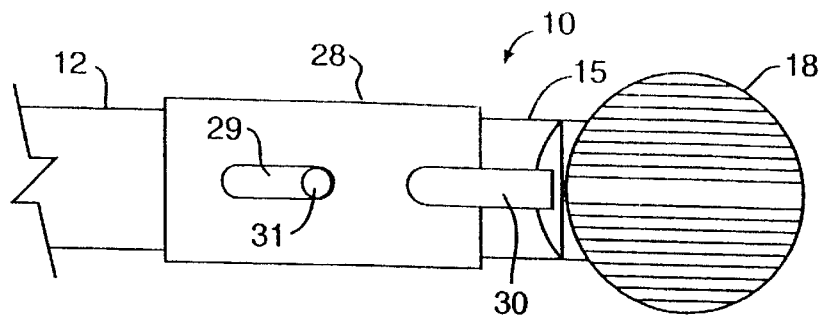
FIG. 1
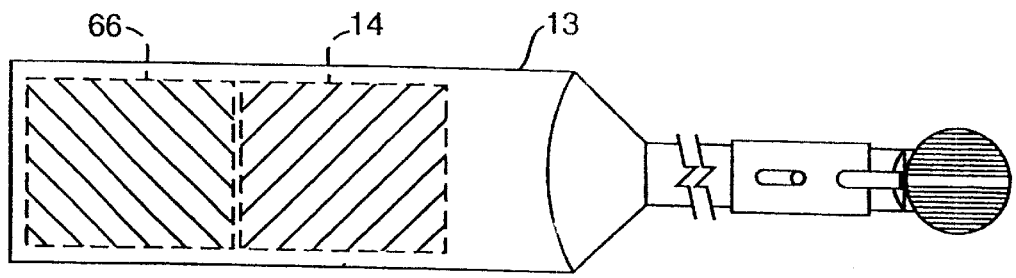
FIG. 1A
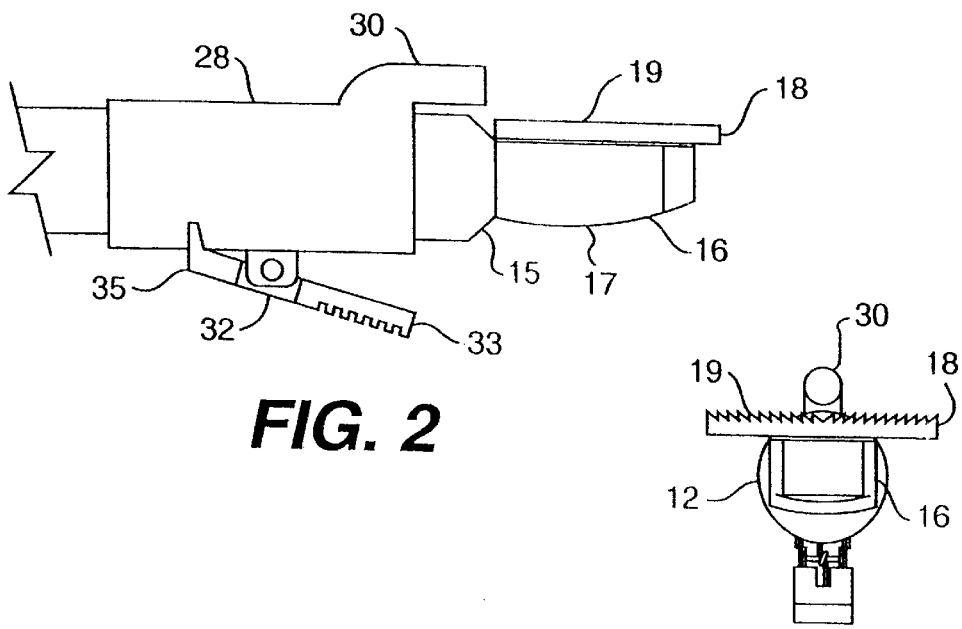
FIG. 2
FIG. 3

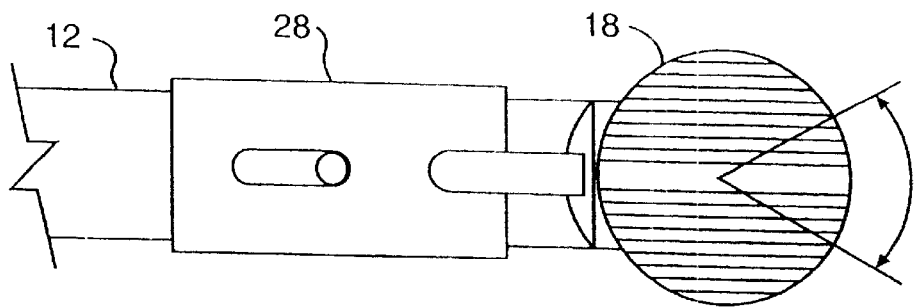
FIG. 4
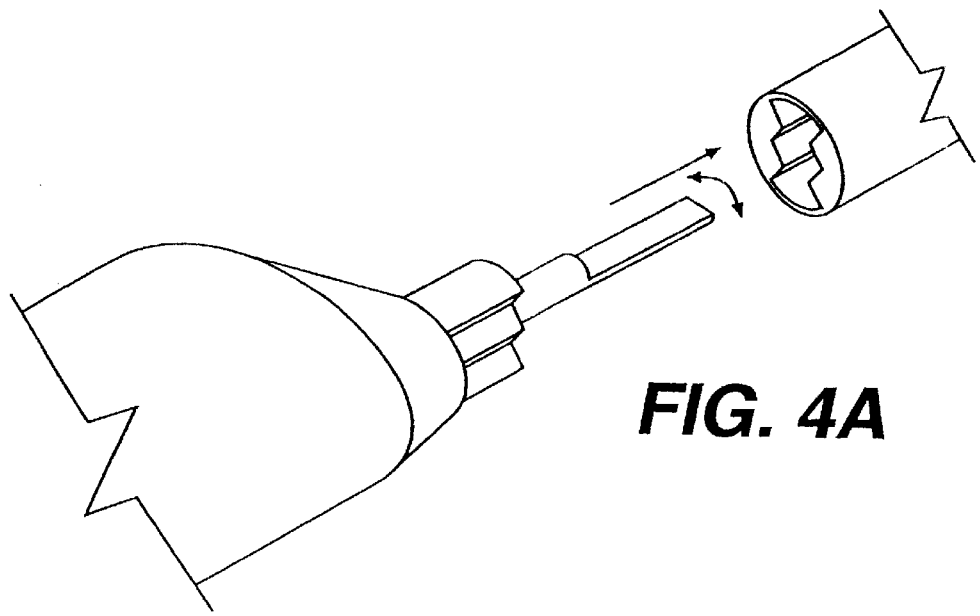
FIG. 4A
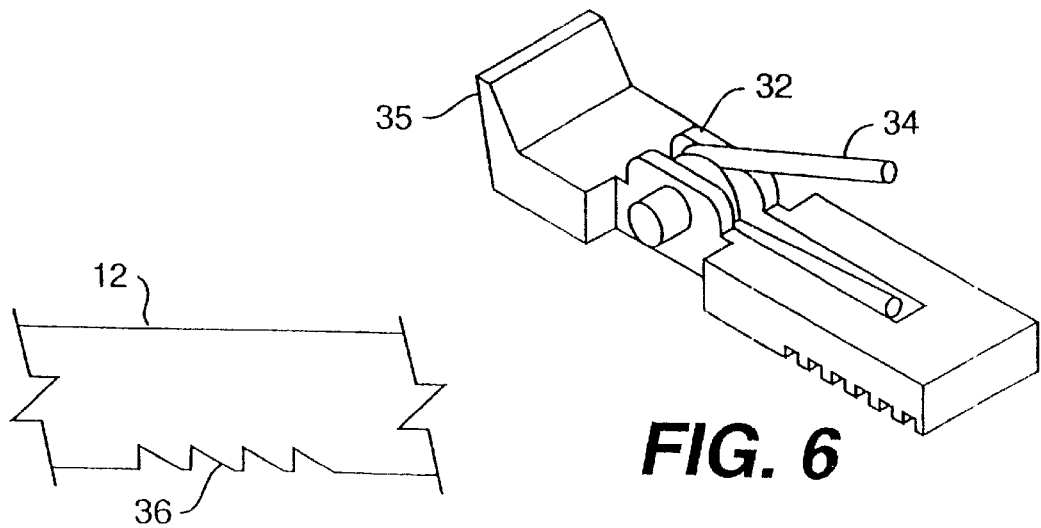
FIG. 6
FIG. 5

DEVICE AND METHOD FOR PREPARING A SPACE BETWEEN ADJACENT VERTEBRAE TO RECEIVE AN INSERT

This is a continuation of application Ser. No. 09/094,036, filed Jun. 9, 1998, now U.S. Pat. No. 6,083,228 all of which are incorporated herein by reference.

FIELD OF THE INVENTION

The present invention relates to a device for insertion into a disc space between adjacent vertebral bodies in the human spine, and a method of working on those portions of the vertebral bodies adjacent that disc space to remove bone material and thereby access vascular bone. The device and associated method forms a surface on each of the vertebral body surfaces that are adjacent the intervertebral disc space, either sequentially, or in an alternative embodiment, simultaneously. The formed surface(s) have a shape and a contour corresponding to an interbody spinal insert to be implanted in the disc space.

BACKGROUND OF THE INVENTION

Inserts for placement between adjacent vertebrae in the spine come in a variety of shapes and sizes and are made of a variety of materials. Such inserts may or may not be designed to promote fusion of the adjacent vertebral bodies. Inserts not intended to participate in or to promote fusion of the adjacent vertebrae, for example an artificial spinal disc, are intended to maintain the spacing between the adjacent vertebrae and to permit relative motion between those vertebrae. Such inserts may or may not include some type of surface treatment or structure designed to cause the vertebrae to attach and grow onto the surface of the insert to thereby stabilize the insert. Another type of insert comprises bone grafts. Such bone grafts are typically intended to participate in and to promote fusion of the adjacent vertebrae. Another type of insert for use in human spinal surgery comprises implants made of selected inert materials, such as titanium, that have a structure designed to promote fusion of the adjacent vertebrae by allowing bone to grow through the insert to thereby fuse the adjacent vertebrae. This last type of insert is intended to remain indefinitely within the patient's spine.

The first known example of this last type of insert (for use in humans) is described in U.S. Pat. No. 5,015,247, which, in its preferred embodiment, discloses a hollow, threaded, cylindrical, perforated fusion implant device made of a material other than and stronger than bone and which is intended to cause fusion of adjacent vertebral bodies. A fusion promoting material, such as cancellous bone for example, is packed within the hollow portion of the implant and participates in the fusion. As used herein, the term fusion defines the growth of bone tissue from one vertebral body across a disc space to an adjacent vertebral body to thereby substantially eliminate relative motion between those vertebrae.

Human vertebral bodies are comprised of a hard outer shell of cortical bone (sometimes referred to as the cortex) and a relatively softer, inner mass of cancellous bone. Just below the cortical bone is a layer referred to as the subchondral plate. The outer shell of cortical bone that is adjacent the disc and the underlying subchondral plate are together herein referred to as the "end plate" and, for the purposes of this application, is hereby so defined to avoid ambiguity. The spinal disc that resides between adjacent vertebral bodies maintains the spacing between those vertebral bodies and, in a healthy spine, allows for relative motion between the vertebrae. At the time of surgery, for example in the instance where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone to grow onto or through an insert that is placed between the vertebrae.

Present methods of forming this space between adjacent vertebrae generally include the use of one or more of the following: hand held biting and grasping instruments known as rongeurs; drills and drill guides; rotating burrs driven by a motor; and osteotomes and chisels. Sometimes the vertebral end plate must be sacrificed as occurs when a drill is used to drill across the disc space and deeper into the vertebrae than the thickness of the end plate. Such a surgical procedure necessarily results in the loss of the hardest and strongest bone tissue of the vertebrae—the end plate—and thereby robs the vertebrae of that portion of its structure best suited to absorbing and supporting the loads placed on the spine by everyday activity. Nevertheless, the surgeon must use one of the above instruments to work upon the adjacent end plates of the adjacent vertebrae to access the vascular, cancellous bone that is capable of participating in the fusion and causing active bone growth, and also to attempt to obtain an appropriately shaped surface in the vertebral bodies to receive the insert. Because the end plates of the adjacent vertebrae are not flat, but rather have a compound curved shape, and because the inserts, whether made of donor bone or a suitable implant material, tend to have a geometric rather than a biologic shape, it is necessary to conform the vertebrae to the shape of the insert to be received therebetween.

It is important in forming the space between the adjacent bone structures to provide a surface contour that closely matches the contour of the inserts so as to provide an adequate support surface across which the load transfer between the adjacent bone structures can be evenly applied. In instances where the surgeon has not been able to form the appropriately shaped space for receiving the inserts, those inserts may slip or be forcefully ejected from the space between the adjacent vertebrae, or lacking broad contact between the insert and the vertebrae, a failure to obtain fusion may occur.

Furthermore, no known prior art device for preparing the vertebral end plates to receive an insert includes a working element that corresponds in shape, size, or contour to the shape of the insert to be implanted. That is, the known devices must be moved from side to side and in and out within the intervertebral space by an amount that exceeds the dimensions of the working element of the device, e.g., the rotating burr of a motor driven routing instrument or the working end of known osteotomes and chisels.

OBJECTS OF THE PRESENT INVENTION

It is an object of the present invention to provide a device and method for quickly, safely, effectively, and accurately working upon a vertebral body end plate adjacent a disc space so as to, while preserving that end plate at least in part, remove bone to produce a receiving surface corresponding in size, shape, and contour to an insert to be implanted between the adjacent vertebrae.

It is a further object of the present invention, in at least certain embodiments, to provide a device capable of simultaneously working upon both of the vertebral body end plates adjacent a disc space to produce opposed receiving surfaces in the adjacent end plates corresponding in size, shape and contour to an insert to be implanted, and in so doing to define the shape to the insert space.

It is a further object of the present invention to provide a vertebral interspace preparation device that, in a preferred embodiment, is capable of working with linear insertion, i.e., insertion along a single axis, and without the need to substantially move the device from side to side within the disc space along a second axis. In such a preferred embodiment, the device has at its working end an abrading element having a width generally corresponding to the width of the insert to be implanted.

It is a further object of the present invention to have a safety mechanism built into the device that limits the depth of insertion of the device into the spine.

It is a further object of the present invention to provide a vertebral interspace preparation device that has interchangeable ends so as to be capable of producing a variety of differently sized and contoured surfaces and shapes within the intervertebral space.

It is a further object of the present invention to have abrading surfaces extending to the leading end of the device such that the device may remove bone along its leading end as it is advanced within the disc space.

These and other objectives of the present invention will occur to those of ordinary skill in the art based on the description of the preferred embodiments of the present invention described below. However, not all embodiments of the inventive features of the present invention need achieve all the objectives identified above, and the invention in its broadest aspects is not limited to the preferred embodiments described herein.

BRIEF DESCRIPTION OF THE DRAWINGS

FIG. 1 is a partial top view of a first preferred embodiment of a device embodying the present invention, which device includes an abrading element having a single abrading surface;

FIG. 1A is a full top view of the device of FIG. 1 illustrating the handle of the device;

FIG. 2 is a side view of the device shown in FIG. 1;

FIG. 3 is an end view of the device shown in FIGS. 1 and 2;

FIG. 4 is a second top view of the device shown in FIG. 1 and also illustrates the preferred range and type of motion of the abrading element;

FIG. 4A is a partial view of the device of FIGS. 1–4 showing a preferred mechanism for connecting the handle to the device shaft;

FIG. 5 is a detailed view of a portion of the device shaft illustrating notches used to hold a stop member in a selected position;

FIG. 6 is a detailed view of a spring-biased lever mechanism that may be used to adjust the position of a stop member;

SUMMARY OF THE INVENTION

Figure 7:
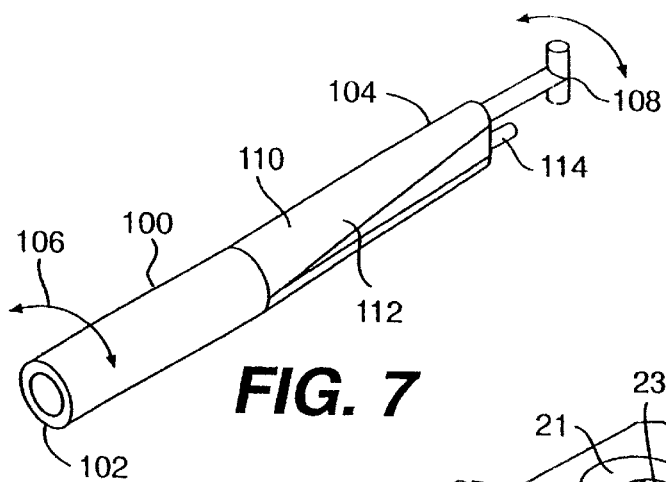
FIG. 7 is a detailed view of a coupling mechanism that may be used to movably couple the drive mechanism to the abrading element.

The device, in its preferred embodiment, generally comprises an abrading element movably and replaceably mounted on the distal end of a shaft, and a depth limiting mechanism to control the depth of insertion of the abrading element into the intervertebral space (i.e., the disc space).

The device also includes a handle that may be detachable from the shaft. As used herein, the term "handle" refers to a portion of the device that a surgeon may grip or otherwise manipulate to guide the working end of the device. That "handle" may, in fact, have multiple purposes. For example, the handle may be a portion of the shaft on which the abrading element is mounted at one end. Alternatively, the handle may be part of a segment that connects the device to a power source, for example, part of a conduit that supplies pressurized gas if the power source is turbine driven. In any event, the term "handle" is used herein in its broadest context to refer to that portion of the device that the surgeon chooses to grasp.

Additionally the shaft may be detachable from the abrading element. The device also includes a drive mechanism for transmitting power to activate, i.e., move, the abrading element, and the drive mechanism is connected to an energy source, e.g., a rechargeable battery, that may be housed within the handle of the device. By way of example only, the drive mechanism may comprise an electric motor or an electromagnetic oscillating mechanism. Or, again by way of example only, the drive mechanism and handle in which it is disposed may comprise the head unit of a gas powered turbine of the type commonly used in other surgical instruments.

In the preferred embodiment, the abrading element is generally as wide as the insert to be implanted between the adjacent vertebral bodies adjacent the disc space. The receiving bed, i.e., the prepared surface of the vertebrae, when formed by the device, will correspond in shape, size, and contour to the corresponding surfaces of the insert to be implanted. By way of example only, the surface produced may be flat or concave, or of some other desired shape and size so as to correspond to the upper or lower vertebrae contacting surfaces of the insert that will be implanted between the vertebrae. The device may also include a leading end that is capable of cutting through bone and/or disc material to form a pocket having a contour corresponding to the forward aspect and leading end of the insert to be implanted.

In a first preferred embodiment, the abrading element includes a single abrading surface that works on one vertebral surface at a time within the disc space.

In a second preferred embodiment, the abrading element includes a pair of opposed, outwardly facing abrading surfaces which lie in planes that may be either parallel to each other or, alternatively, convergent to each other. This embodiment of the present invention offers the further benefits of saving time by simultaneously preparing both of the vertebral end plates adjacent a disc space. The second embodiment not only includes the ability to simultaneously create two opposed surfaces, but also to shape the three-dimensional space that will be created between the adjacent vertebrae, which shape can be made to conform to the desired lordosis of that portion of the spine that will receive the insert.

However, the abrading element of the present invention is not limited to being a unitary, one piece construction, regardless of the number of abrading surfaces the abrading element may have. The abrading element may comprise multiple pieces that, by way of example and not limitation, are mountable on the end of the device to, in combination, define the overall shape of the abrading element and its abrading surface or surfaces. Thus, the term "abrading element" is used herein to refer to both a unitary, one piece construction or a multi-piece construction.

Thus, the present invention provides a device and method for preparing a disc space between adjacent vertebral bodies to receive an insert, and prepares that disc space by removing a portion of the end plate of the vertebrae adjacent that disc space to form predetermined surfaces in the end plates. The prepared surfaces are sized and contoured to have broad intimate contact with the insert to be implanted between the adjacent vertebrae, which broad contact provides for increased implant stability. This broad area of intimate contact between the vertebrae and the insert promotes bone ingrowth from the vertebrae into the insert, and also provides a broad area over which to support the incumbent loads so as to minimize the risk of vertebral collapse or subsidence of the insert into the vertebra.

The abrading element is mounted on the mounting member and may be removable and interchangeable. In such an embodiment, the mounting member may be, but does not have to be, attachable to a shaft that is attachable to the handle. The abrading element and the mounting member may be separable from each other. Alternatively, the abrading element and the mounting member may, together, be removable from the handle. Various configurations of the abrading element and its abrading surface or surfaces can be used to form various contours in the adjacent vertebral bone structures.

In the instance where the abrading element has one abrading surface, the opposite surface of the abrading element, or the opposite surface of the mounting member, may be specifically designed to be non-abrading to the opposed adjacent vertebral end plate. Such a non-abrading surface may be designed to provide a mechanical advantage (such as achieved with a fulcrum) to allow the surgeon to increase the pressure of the abrading surface against the end plate being worked on, and, further, may be curved so as to be centering within the disc space by contact with a vertebral surface.

While the preferred embodiment of the present invention is discussed and disclosed herein with respect to creating a space between adjacent vertebrae in the spine, the present invention is not limited to a device for creating a space between adjacent vertebrae, but can also be used in other portions of the body where it is desirable to place an insert between adjacent bone structures. Furthermore, and as alluded to above, an embodiment of the present invention may have upper and lower abrading surfaces that are in angular relationship to each other so as to, for example, match the natural lordotic curvature of the human spine at the location of the vertebrae to be operated upon. Similarly, certain of the abrading surfaces of the abrading element may be configured with a convex, or even compound, geometry so as to form surfaces in the adjacent bone structures having a desired contour. Additionally, sequentially larger ones of the abrading element, or mounting member, may be used to form the desired space in a step-wise fashion, or the abrading element may be sized to substantially match the final desired width of the surface to be formed in the vertebral end plate. Furthermore and also as noted above, the abrading element may be configured with a sharpened leading edge to allow the abrading element to "forward cut" as it is inserted between the adjacent vertebrae. In this manner, progressive insertion of the abrading element between the vertebrae can be facilitated.

While the present invention has been generally described above, and the preferred embodiments of that invention will be described in detail below, neither that general description nor the detailed description limits the scope of the present invention. That scope is defined solely by the claims appearing at the end of this patent specification.

DETAILED DESCRIPTION OF THE PRESENTLY CONTEMPLATED EMBODIMENTS

With reference to FIGS. 1 and 1A, a first embodiment of the present invention comprises a disc space preparation device generally referred to by numeral 10. Device 10 includes a shaft 12 and a handle 13. Handle 13 may be formed with any number of known shapes designed to make the surgeon's grip on the handle more secure or comfortable. Similarly, handle 13 may include a soft rubber covering or may be formed, at least partially, of a material designed to promote a secure grip of the surgeon's hand on the handle. Those of ordinary skill in the art will recognize the many types of surface configurations or materials of which the handle can be made to achieve these goals.

With continued reference to FIGS. 1 and 1A, disposed within handle 13 is a drive mechanism diagrammatically depicted by box 14. Although in the embodiment of the device shown in FIGS. 1 and 1A the drive mechanism 14 is disposed within handle 13, it need not be disposed in the handle. The drive mechanism may be disposed completely or partially outside of the handle, for example, where the drive mechanism is a gas powered turbine element such as is used in some known surgical instruments. Drive mechanism 14 is operably connected to the proximal end of shaft 12 and is capable of moving an abrading element 18 disposed at a distal end 15 of shaft 12. Abrading element 18 has an abrading surface 19. Drive mechanism 14 moves abrading element 18 at a sufficiently high rate to quickly and efficiently cause abrading surface 19 to form the desired space and the desired surface contours in the adjacent vertebral bone structures. As illustrated in FIG. 2, the abrading element 18 is mounted on a mounting member 16 disposed at the distal end 15 of shaft 12. In this embodiment, the mounting member is fixed to shaft 12 and only the abrading element moves. However, many alternative mechanisms for mounting the abrading element on the device are possible within the scope of the present invention, including a mechanism wherein mounting member 16 is movably attached to shaft 12 and the drive mechanism moves both the mounting member and the abrading element attached thereto. Also, mounting member 16 may be designed with a surface 17 on the side of the mounting member 16 opposite abrading element 18. Surface 17 is designed, in the embodiment shown, to bear against the end plate that is opposite the end plate being worked on by abrading element 18. In this manner, surface 17 provides a bearing surface that the surgeon may use to gain a mechanical advantage (such as with a lever) to contact abrading surface 19 of abrading element 18 against the end plate being worked on. Additionally, surface 17 may be curved as shown in FIG. 2, or otherwise shaped, to contact one end plate and, thereby, center or otherwise position abrading element 18 in the disc space.

As presently contemplated, the motion of the abrading element may be vibratory, reciprocatory, oscillatory, or rotary. In the first preferred embodiment of device 10, the motion of the abrading element is rotary in a clockwise then counterclockwise direction through a preferred range of motion of between 20° to 45°, as illustrated in FIG. 4. Whatever type and range of motion is selected for the abrading element, it will likely, although not necessarily, be in a direction that is generally parallel to the plane of the surface to be formed in the vertebral end plate. However, since the shape of that surface contour is not necessarily flat, neither is the direction of the motion of the abrading element necessarily parallel to all points on that desired surface contour.

By way of example and not limitation, the drive mechanism may comprise a magnetic driver of the type described in U.S. Pat. No. 5,263,218. Alternatively, the drive mechanism may take the form of a mechanical drive utilizing a cam mechanism such as described in U.S. Pat. No. 5,383,242. Additionally, drive mechanisms used in known surgical power milling apparatus may also be used. As presently contemplated, the drive mechanism should be capable of moving the abrading element and its abrading surface or surfaces at a speed sufficient to abrade the hard cortical bone of the vertebral end plate. The working range and speed of motion of the drive mechanism will be readily selected by those of skill in the art.

In one embodiment of the present invention utilizing reciprocating motion, the stroke or amount of reciprocating movement is relatively small and can be selected, as desired to achieve the purpose of abrading the adjacent bone structures. That stroke may be selected based on the relative strength of the bone structures to be abraded, the relative strength of the material forming the abrading element, and the type of surface roughening formed on one or more surfaces of the abrading element. This relatively small reciprocating movement of the abrading element results in a tightly controlled excursion area between the adjacent vertebrae being prepared to receive an insert. In contrast, a motorized burr must be moved free hand and in a side-to-side motion within the disc space by the surgeon to form a space to receive an insert. Thus, use of such a motorized burr does not provide a way of forming a precise surface shape in the vertebral end plate. Additionally, because the motorized burr rotates in a single direction, it may catch on a piece of the vertebra and cause the burr to jerk forcefully out of the intervertebral space. Such an occurrence will not happen with the device 10 because of the controlled excursion of the device.

In the first embodiment of the present invention described herein, drive mechanism 14 is powered by a rechargeable battery illustrated as box 66 in FIG. 1A. Battery 66 is also preferably located within handle 13 of device 10. However, the present invention is not limited to use with a rechargeable and/or replaceable battery 66, but may also be configured to run on any standard electrical source, such as 110 volt, 60 cycle power sources, with or without the accompanying use of a transformer to reduce that voltage as may be necessary and desirable. Alternatively, the drive mechanism may comprise a gas turbine mechanism as is common for many types of powered surgical instruments. The particular power source that powers drive mechanism 14 does not form a part of the present invention except to the extent it is adapted to achieve the appropriate and desirable amount of movement of the abrading element.

Referring now to FIG. 2, which shows a portion of device 10 in side view, mounting member 16 extends from the distal end 15 of shaft 12. As described below with reference to FIGS. 7–10, the mounting member may be configured to house a portion of a coupling mechanism that, in turn, couples drive mechanism 14 to an abrading element 18 to move the abrading element in at least one degree of freedom while the mounting member remains stationary relative to the handle. The term "degree of freedom" is used herein in its ordinary sense to refer to motion in a standard three-dimensional environment. That three dimensional environment may be defined by X, Y, and Z axes. In such a three-dimensional environment, 6 degrees of freedom exist: translational motion along each of the X, Y, and Z axes, and rotational motion about each of the X, Y, and Z axes. Thus, drive mechanism 14 is operable to move abrading element 18 in a reciprocating, oscillating, or vibrating motion transversely along one or more of the X, Y, and Z axes. Alternatively, or in conjunction, drive mechanism 14 may be configured to move abrading element 18 around one or more of the X, Y, or Z axes. Of course, for purposes of achieving the objectives of the present invention, it may not be necessary that the drive mechanism reciprocate or oscillate mounting member 16 in anything more than a single degree of freedom.

Figure 8:
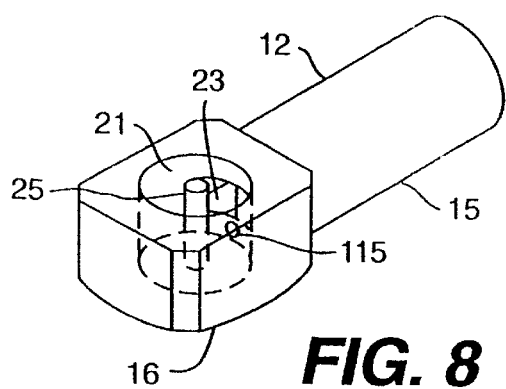
FIG. 8 is a detailed view of the mounting member disposed at the distal end of the device shaft.
Figure 9:
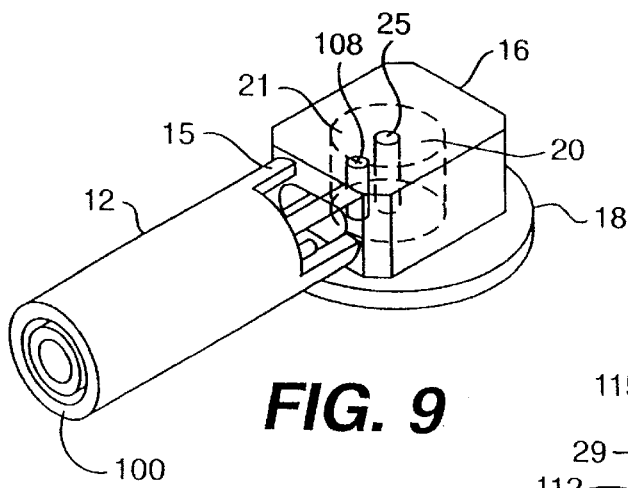
FIG. 9 is a further detailed view of the coupling mechanism and mounting member illustrated in FIGS. 7 and 8.
Figure 10:
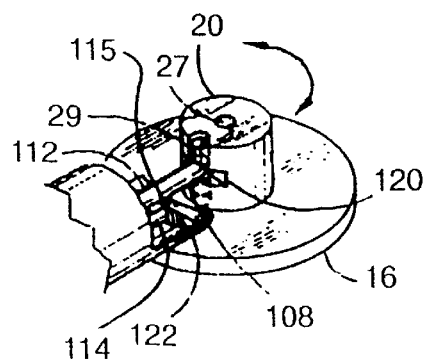
FIG. 10 is a detailed view illustrating a preferred way of movably connecting the coupling mechanism to the abrading element.

Referring now to FIGS. 7–10, in a present preferred embodiment, abrading element 18 includes a projection 20 (as best seen in FIG. 10) that is to be received in a corresponding aperture 21 formed in mounting member 16 (as best seen in FIG. 8). Mounting member 16 may be fixedly disposed on distal end 15 of shaft 12. Alternatively, mounting member 16 may be removably attached to distal end 15 of shaft 12. In the present embodiment, a coupling mechanism is used to couple abrading element 18 to mounting member 16 and to the drive mechanism. FIG. 10 illustrates that coupling mechanism with mounting member 16 removed to show in clearer detail the coupling mechanism.

With reference to FIGS. 7 and 9, the coupling mechanism in the first preferred embodiment of the present invention comprises a generally tubular member 100 received within a hollow, longitudinal aperture of shaft 12. Tubular member 100 includes a proximal end 102 and a distal end 104. A T-shaped connector 108 is configured at the end of a drive rod 112. Drive rod 112 is adapted to be received within a corresponding aperture 110 in tubular member 100. A pivot rod 114 extends from the distal end 104 of tubular member 100 and is adapted to fit in a corresponding hole 115 formed in mounting member 16 at the end of shaft 12.

With reference to FIG. 8, mounting member 16 includes a central aperture 21 and an oblong slot 23 formed through a wall of mounting member 16. Slot 23 is configured to allow connector 108 to pass through when the connector is turned (as illustrated by the arrows in FIG. 7) so that the branches forming the "T" extend laterally. Mounting member 16 also includes a post 25 that projects into aperture 21. Post 25 is sized to mate with an aperture 27 formed in projection 20 of abrading element 18 as shown in FIG. 10. Projection 20 is also formed with a slot 29 designed to receive connector 108 as described below.

With reference to FIG. 9, tubular member 100 fits within shaft 12 with connector 108 extending from distal end 13 of the handle. Projection 20 of abrading element 18 is inserted into aperture 21 of mounting member 16 such that post 25 fits into aperture 27 of projection 20. Connector 108 is initially rotated such that its "T" branch fits through slot 23 of mounting member 16 and then is rotated 90° as shown by the arrows in FIG. 7. With the "T" branches of connector 108 extending parallel to post 25, projection 20 of abrading element 18 fits into aperture 21 of mounting member 16 such that connector 108 fits into slot 29, and post 25 fits into aperture 27.

FIG. 10 shows the same structure as FIG. 9 but with mounting member 16 removed for purposes of better illustrating the mating of connector 108 with slot 29. As shown in FIG. 10, pivot rod 114 fits into a mating aperture 115 formed at the distal end of shaft 12, and projection 20 includes a second slot 120 formed laterally from slot 29. Slot 120 is configured to allow connector 108 to toggle back and forth as tubular member 100 is reciprocatingly pivoted about pivot rod 114 by the device's drive mechanism. This "toggling" action of member 100 about pivot rod 114 moves T-shaped connector 108 and abrading element 18 in the direction indicated by the double headed arrow in FIG. 10.

Of course, many variations exist for mechanisms to couple the drive mechanism 14 to abrading element 18. The coupling mechanism described above is provided by way of example and not limitation.

In the embodiment described, mounting element 16 may interchangeably receive various ones of abrading element 18. Thus, abrading element 18 may be quickly and easily attached to and detached from mounting member 16 during surgery. While in the preferred embodiment the abrading surface of the abrading element is selected to have a width that is substantially the same as the width of the surface to be formed in the vertebral end plate (to eliminate any need to move the abrading element side to side in the disc space as noted earlier), a surgeon might also elect to use an abrading element that is smaller in width than the ultimate desired width of the surface to be formed. Thereafter, the surgeon may use successively larger abrading elements 18 until she arrives at the desired dimensions of the space formed between the adjacent bone structures. This approach also eliminates any need to significantly move the abrading element in a side to side path within the disc space.

Referring back to FIGS. 1 and 1A, device 10 includes at least one stop member 28 adjustably disposed on mounting element 16 to limit the travel of the abrading element into the adjacent bone structures. Stop member 28 includes an abutment 30 that will eventually contact the vertebrae to limit travel of the abrading element 18 as the abrading element forms the space between the adjacent vertebrae. Stop member 28 is not limited to a single abutment. Two or even more abutments may be formed around the circumference of stop member 28 and the leading edges of such multiple abutments may be configured to terminate at different positions relative to shaft 12. Other mechanisms for limiting the depth of insertion of the device into the disc space are possible, and this example is provided by way of illustration.

In the embodiment of stop member 28 shown in FIGS. 1, 2, and 3, a slot 29 is formed in stop member 28 and an extension 31 projects from shaft 12 through slot 29. Slot 29 is dimensioned to correspond to the desired maximum amount of adjustment of the stop member relative to the handle. As shown in FIG. 2, and in FIGS. 5 and 6, stop member 28 is held at a desired position on shaft 12 by spring-biased lever 32. Lever 32 includes an actuator end 33 with grooves, notches, knurls, or other surface preparation that is pushed toward shaft 12 against the bias of spring member 34 to lift engaging end 35 of lever 32 away from shaft 12. Engaging end 35 is configured to mate with notches 36 formed in shaft 12 as shown in FIG. 5. Notches 36 in shaft 12 are not visible in FIG. 2 since they are covered by stop member 28. Step member 28 is also formed with an opening sized to allow engaging end 35 of lever 32 to fit in notches 36. Numerous other structures for holding stop member 28 at a desired position on shaft 12 are possible, and spring biased lever 32 is provided in this embodiment of the present invention by way of example and not limitation. For instance, shaft 12 may include threads on a portion of its outer surface to receive a threaded adjusting collar that will lock stop member 28 in a desired position.

Figure 21:
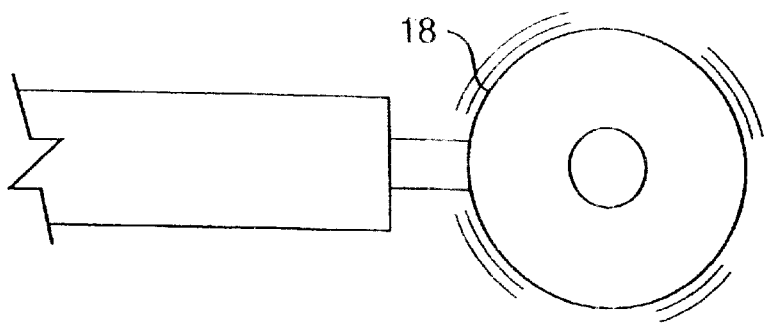
FIG. 21 illustrates an alternative path of motion possible for an abrading element according to the present invention.
Figure 22:
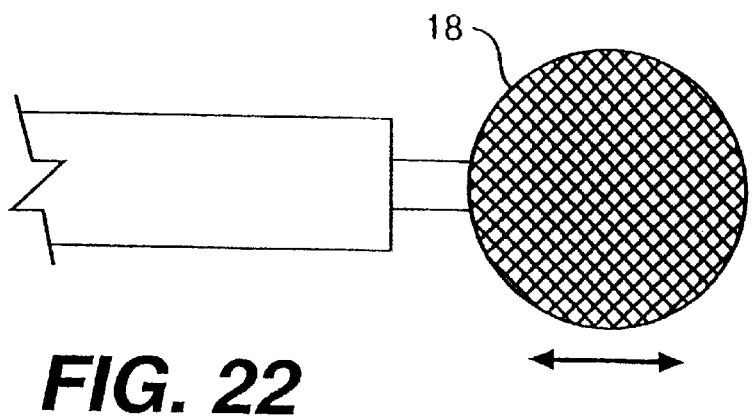
FIG. 22 illustrates a further alternative path of motion possible for the abrading element.

With reference to FIGS. 21 and 22, examples of the types of motion through which abrading element 18 may be moved are illustrated. In FIG. 21, the motion is vibratory in a plane generally parallel to the abrading surface of the abrading element. In FIG. 22, the motion is linear and reciprocating as indicated by the double headed arrow of that figure. Alternatively, the motion may comprise slight rotation about a pivot point near distal end 15 of shaft 12 such that the oscillation is arcuate about an axis extending into and out of the sheet of paper on which FIGS. 21 and 22 are illustrated. Other motions such as full and complete rotation as described below with reference to the second preferred embodiment are also useful.

Any of these types of motion will be adequate to cause the abrading surface or surfaces of abrading element 18 to abrade adjacent bone structures to thereby form the appropriately sized and dimensioned space between those bone structures for receiving an insert. In this regard, at least one or more of the surfaces of abrading element 18 is roughened such that it can abrade the adjacent bone structures.

Figure 11:
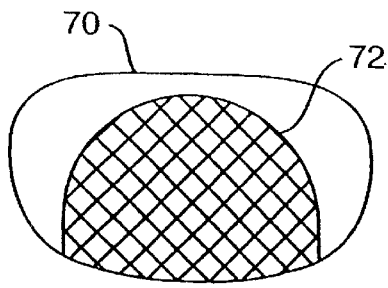
FIG. 11 is top view of a first vertebral body having a surface prepared in one of the end plates by a device incorporating the present invention.
Figure 12:
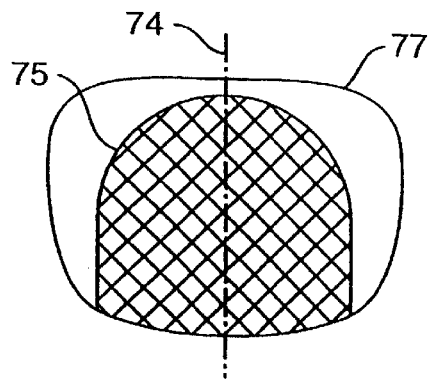
FIG. 12 is a top view of a second vertebral body, different than that shown in FIG. 11, having a surface prepared in one of the end plates by a device incorporating the present invention.
Figure 14:
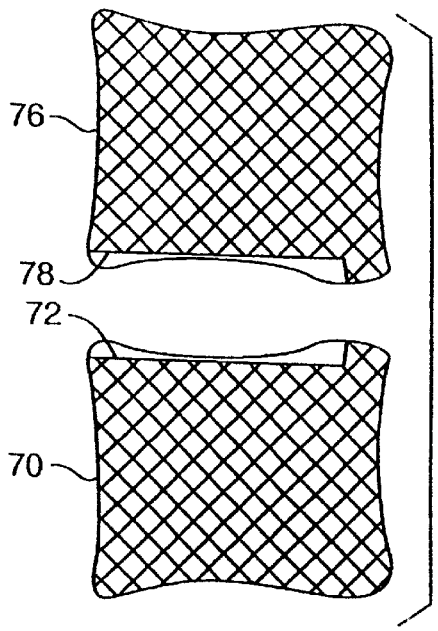
FIG. 14 is a cutaway side view of adjacent vertebral bodies having their respective adjacent end plates prepared by a device incorporating the present invention to form a space configured to receive an insert.
Figure 13:
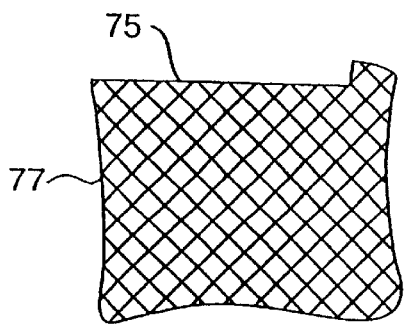
FIG. 13 is a cutaway side view of the vertebral body shown in FIG. 12.

FIGS. 11, 12, 13, 14, and 15 illustrate various views of vertebral bodies that have been worked on by a device incorporating the present invention. The cross-hatching in these figures represents the softer, blood rich cancellous bone of the vertebrae beneath the harder, outer cortical bone shell. FIG. 11 shows a top view of a first vertebral body 70 with a surface 72 formed by a circular abrading element 18 as shown in FIG. 1. The width of surface 72 formed on first vertebral body 72 closely matches the width of an abrading element 18 that was advanced into the disc space along a single front to back axis. A second vertebral body 77 has a greater depth than vertebral body 70. The second vertebral body 77 shown in FIG. 12 has a surface 75 formed by extending abrading element 18 deeper into the distal interspace along front-to-back axis 74. FIG. 13 illustrates a cutaway side view of the vertebral body shown in top view in FIG. 12. FIG. 14 shows a cutaway side view of adjacent vertebral bodies 70 and 76 that have had surfaces 72 and 78 formed in their respective adjacent end plates. Note that, as shown in exaggerated view in FIG. 15, the vertebral end plate surface is prepared to a uniform shape, which while preserving the deeper portions of the end plate, also forms a socket depressed from the hard cortical uprisings of bone such as the uncovertebral joints 80. Recognize that the depth of this remaining end plate is exaggerated in FIG. 15 to illustrate this result of using the present invention. This remaining portion of the more cortical rim 80 assists in retaining the insert in the desired position between the adjacent vertebrae by acting as an abutment preventing lateral or posteriad movement of the insert. The prepared faces of these abutment portions of the vertebral end plate also increase the surface area of contact between the insert and the vertebral body.

Figure 15:
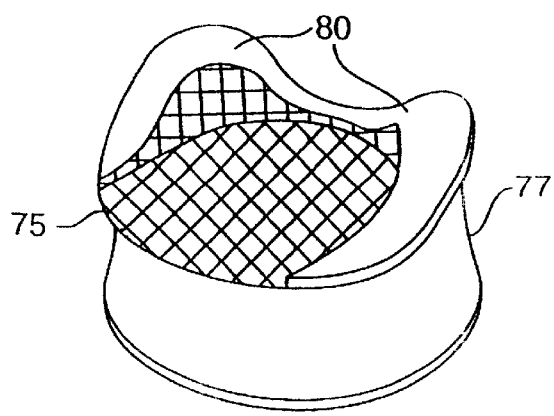
FIG. 15 is an exaggerated perspective view of the vertebral body illustrated in FIG. 12 showing the formation of the receiving surface in the vertebral end plate.
Figure 15A:
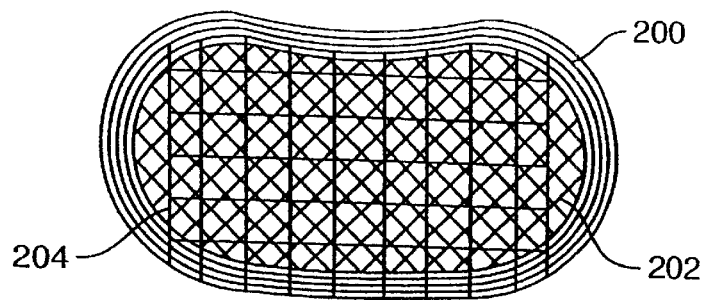
FIG. 15A is a top view of a section of a human spine illustrating the portion of the disc that is typically removed to accommodate the implantation of an intervertebral insert.

FIG. 15A illustrates, in top view, the ideal portion of a disc that is removed to accommodate implantation of the insert. In FIG. 15A, the annulus fibrosus is illustrated with rings 200 extending around the periphery of the intervertebral disc space. Inside the annulus fibrosus is the nucleus pulposus 202 illustrated in cross-hatching. The general area and volume of the nucleus pulposus to be removed with the device of the present invention is illustrated with additional cross-hatchings 204. The preferred dimensions of the space created by the device is generally not as wide as the entire nucleus pulposus.

Figure 16:
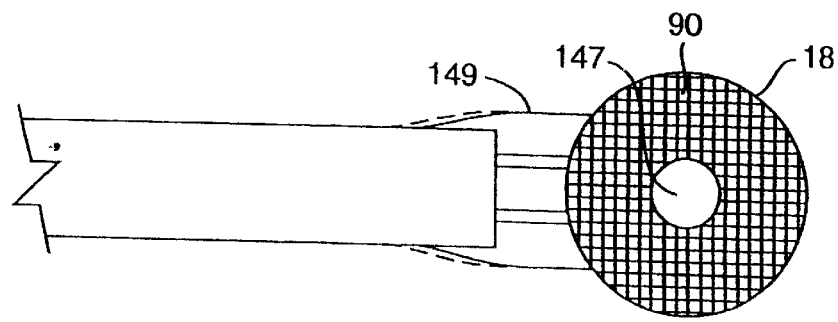
FIG. 16 is a top view of a second preferred embodiment of a device embodying the present invention, which device includes an abrading element having two abrading surfaces.
Figure 17:
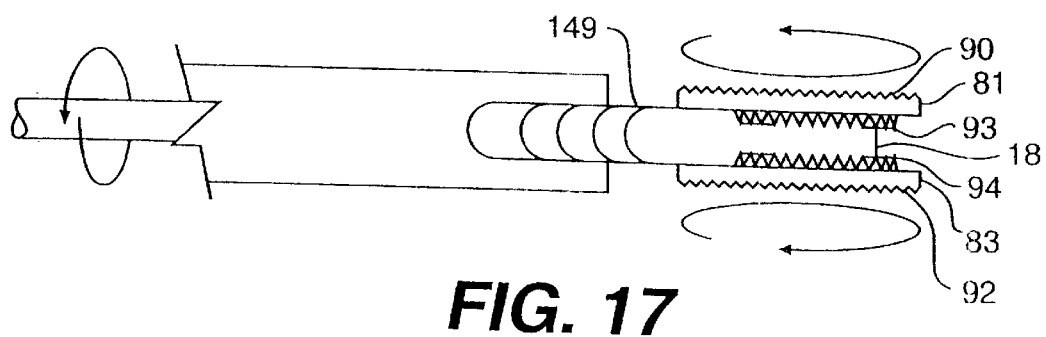
FIG. 17 is a side view of the device shown in FIG. 16.
Figure 17A:
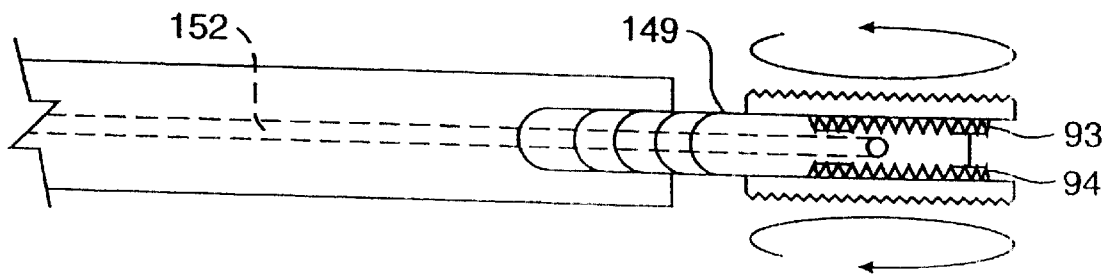
FIG. 17A is a side view of the device shown in FIG. 17.
Figure 17B:
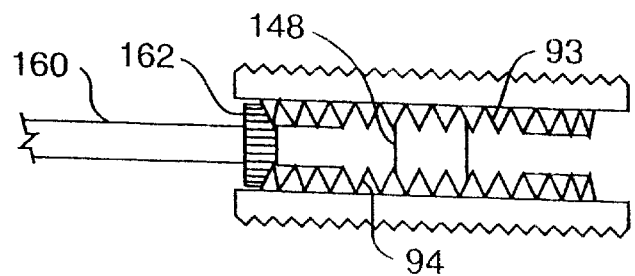
FIG. 17B is a detailed view of one possible drive mechanism that may be used with the second embodiment of the present invention.

Referring now to FIGS. 16 and 17, a second embodiment of the present invention is shown wherein abrading element 18 includes two abrading surfaces: an upper abrading surface 90 and a lower abrading surface 92. FIG. 16 is a top view of such a device and FIG. 17 is a side view. In this embodiment, abrading element 18 includes two disc shaped members, 81 and 83, that are mounted on the distal and of the device by a recessed screw 147 and screw shaft 148 as described below. Abrading surface 90 is formed on one side of disc-shaped member 81, and abrading surface 92 is formed on one side of disc-shaped member 83. Thus, the abrading element 18 illustrated in FIGS. 16 and 17 provides an example of an instance where the abrading element comprises multiple pieces that fit together to form the abrading element. As previously described, the present invention contemplates unitary, one piece constructions for the abrading element as well as multi-piece constructions. In the embodiment of the present invention shown in FIGS. 16 and 17, the upper and lower disc-shaped members 81 and 83 and their associated abrading surfaces may be rotated in opposite directions so as to counteract and balance any torque applied to the shaft and handle of the device as the abrading element digs into and abrades the vertebral end plates. This counter-rotation of the members 81 and 83 also prevents the device from being pulled to one side as the vertebral end plates are being worked on. This counter-rotating motion of the two members 81 and 83 is illustrated by the arrows in FIG. 17 and may be achieved, as illustrated in FIG. 17B, by using a spinning drive rod 160 that extends through shaft 12 and is configured with a gear 162 at its distal end that engages with mating gear teeth 93 and 94 formed on respective ones of disc-shaped members 81 and 83 as shown in FIGS. 17A and 17B. Disc shaped members 81 and 83 may be attached to the end of shaft 12 by a recessed screw 147 that is received in a mating, threaded screw shaft 148 as shown in FIG. 17B. Thus, in this second embodiment, the mounting member comprises threaded screw shaft 148 and recessed screw 147 disposed at the distal end of a tapered extension 149 that protrudes from shaft 12.

Figure 16A:
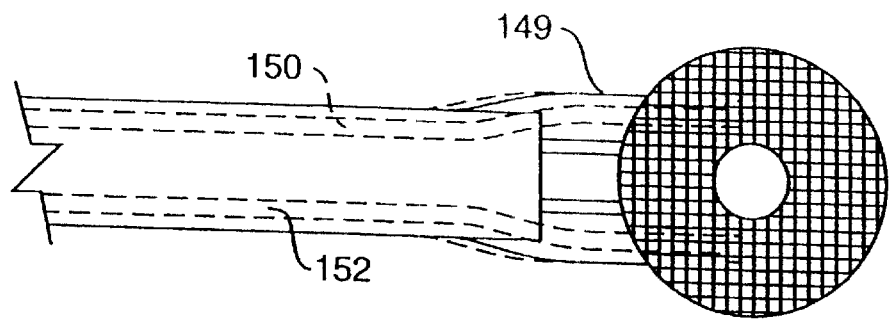
FIG. 16A is a top view of the device of FIG. 16 illustrating irrigation and suction tubes that may be incorporated into the device.

FIGS. 16A and 17A show a further enhancement to the device shown in FIGS. 16 and 17 wherein the shaft 12 also includes an irrigation tube 150 and a suction tube 152 that may be formed within, or outside of, shaft 12. These irrigation and suction tubes may be connected to appropriate sources of irrigation fluid and a source of vacuum, respectively, to efficiently irrigate and clear the surgical site during use of the device.

Figure 20:
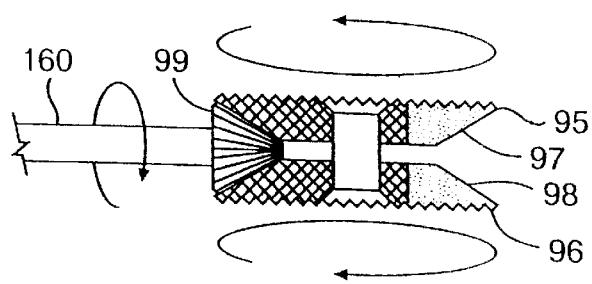
FIG. 20 shows an alternative embodiment of a mechanism for driving an abrading element.

Alternatively, and as shown in FIG. 20, upper and lower disc-shaped members 94 and 96 may be formed with inwardly sloping, ramped surfaces 97 and 98 that engage a cone-shaped driver 99 disposed on the distal end of a rotating drive rod 160 to turn the upper and lower abrading surfaces in opposite directions as the drive rod spins about its axis. Alternatively, the lower surfaces of the abrading element 18 and the cone-shaped driver can be radially splined to engage one another. Such a dual surface abrading element can simultaneously work on both adjacent end plates of adjacent vertebrae. Abrading member 18 having such dual abrading surfaces can even be constructed such that the distance between the abrading surface is adjustable to accommodate variations in the height of the disc space. By way of example and not limitation, paired, wedge-shaped blocks may be disposed between the abrading surfaces and an adjusting screw can be provided to extend through threaded apertures in each wedge-shaped block. As the adjusting screw is turned, the wedge-shaped blocks move relative to one another to change the distance between the abrading surfaces.

Figure 18:
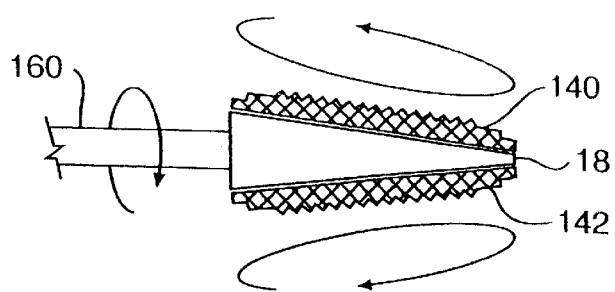
FIG. 18 is an alternative embodiment of an abrading element having two abrading surfaces, which abrading surfaces are inclined relative to one another to form a space between the adjacent vertebral bodies that approximates the lordotic curvature of a human spine at the location that will receive the interbody insert.

In a still further embodiment of the present invention as illustrated in FIG. 18, the abrading element 18 may have upper and lower abrading surfaces 140 and 142 that are angled or tilted relative to each other. The degree of angle or tilt may be selected to match the natural lordotic curvature of the spine at the location of the vertebrae to be worked on.

Figure 19:
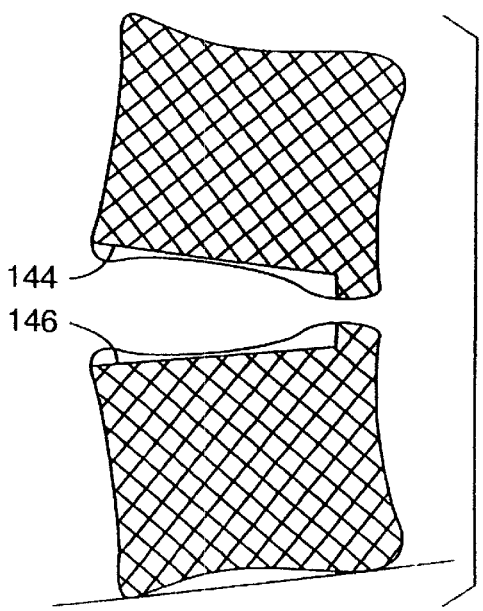
FIG. 19 is a cutaway side view of adjacent vertebral bodies showing a lordotically configured space created between the vertebrae by the abrading element shown in FIG. 18.

The distance between the upper and lower abrading surfaces 140 and 142 in this embodiment may also be adjustable to accommodate differing disc heights between the vertebrae. Such angled abrading surfaces may also be driven in counter rotation by drive rod 160 as shown by the arrows in FIG. 18. As illustrated in FIG. 19, the slope of the surfaces 144 and 146 formed in the adjacent vertebrae by the abrading element shown in FIG. 18 matches the lordotic curvature of the spine at that location.

Figure 23:
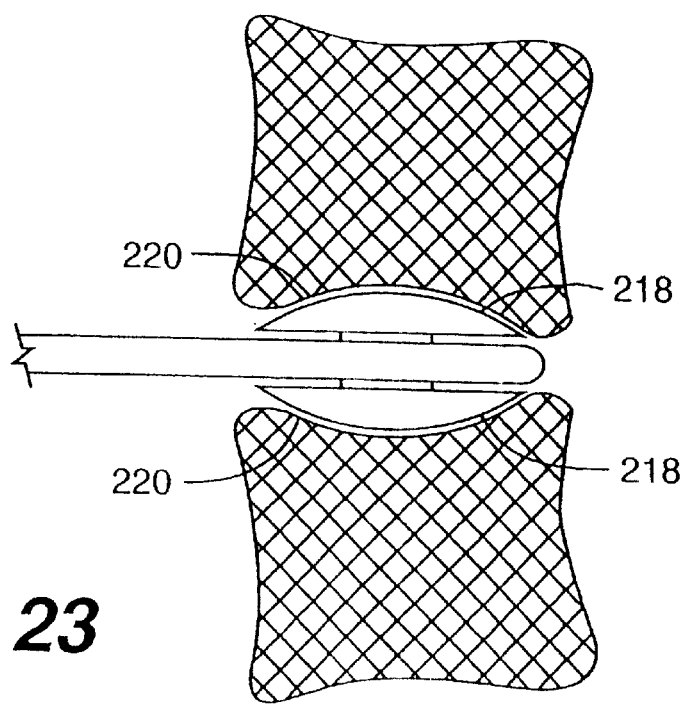
FIG. 23 illustrates an alternative configuration of the abrading element suitable for creating concave insert receiving surfaces on the adjacent vertebral end plates.

Numerous other configurations of abrading element 18 are possible within the scope of the present invention. For example and with reference to FIG. 23, abrading elements 218 may be convex to form concave receiving surfaces 220 in the vertebral end plates. The geometry and configuration of the shapes of the abrading elements can be matched to the desired shape and configuration of the space which the surgeon intends to create between adjacent bone structures and to the desired contour of the surfaces created in the bone structures.

Additionally, the abrading surface of abrading element 18 may be configured as roughenings, knurls, ridges, small pyramid shaped projections, or any other surface configuration that is capable of abrading the bone structures.

Where only one surface of the abrading element is configured to abrade an end plate of the vertebral body, an opposite surface (or the opposite surface of mounting member 16 as illustrated by element 17 in FIG. 2) may be configured to be supported by the adjacent end plate without causing any significant abrasion of that adjacent end plate. In such an instance, the non-abrading surface of the abrading element, or surface 17 of mounting member 16, may be configured to allow the surgeon to achieve a mechanical advantage that increases the bearing pressure of the abrading surface against the end plate being worked on, and also to locate and center the device. In this manner, one adjacent end plate provides mechanical support to the device while the device works on the adjacent end plate. After an appropriate surface is formed on one end plate, the device can be turned 180° to use the abrading surface on the other end plate.

Since any device incorporating the subject matter of the present invention is designed to be used within a surgical theater, it is desirable that the device be susceptible of sterilization by any one of many known expedients. In this regard, handle 12 of device 10 may be waterproof such that the device can be sterilized.

Although various embodiments of the present invention have been disclosed for purposes of illustration, it will be understood by those of ordinary skill in the art that changes, modifications, and substitutions may be incorporated in these embodiments without departing from the spirit or scope of the present invention as defined by the claims, which follow.

I claim:

1. An apparatus for preparing an implantation space in the human spine to receive an insert between adjacent vertebral bodies, comprising:
   a handle;
   a shaft operably connected to said handle,
   a drive mechanism adapted to be operably connected to a power source; and
   an abrading element operably coupled to a distal end of said shaft for movement by said drive mechanism, said abrading element being moved in a direction different than which said shaft is moved, said abrading element having at least one abrading surface selected to create a predetermined surface contour of the adjacent vertebral bodies as said abrading element is moved by said drive mechanism.

2. The apparatus of claim 1, wherein said abrading surface includes teeth formed thereon to cooperatively engage said drive mechanism, said drive mechanism and said teeth being configured such that said abrading surface is rotated by said drive mechanism.

3. The apparatus of claim 1, further comprising a second abrading surface.

4. The apparatus of claim 3, wherein said abrading surfaces are rotated in opposite directions by said drive mechanism.

5. The apparatus of claim 3, wherein said abrading element has at least a top abrading surface and a bottom abrading surface.

6. The apparatus of claim 3, wherein said abrading surfaces are outwardly facing, and said abrading surfaces are inclined relative to one another.

7. The apparatus of claim 1, wherein said abrading element includes at least two abrading surfaces for simultaneously creating predetermined surface contours on the respective end plates of the adjacent vertebral bodies.

8. The apparatus of claim 1, wherein said abrading element includes a non-abrading surface formed on a side of said abrading element opposite said abrading surface, said non-abrading surface being configured to allow a surgeon to increase the pressure of said abrading surface against one of the adjacent vertebral bodies.

9. The apparatus of claim 1, wherein said abrading surfaces is convex.

10. The apparatus of claim 1, wherein said abrading element has a front surface and is tapered outwardly from said front surface toward said handle.

11. The apparatus of claim 1, wherein said abrading element includes a leading edge configured as a bone cutting surface.

12. The apparatus of claim 1, wherein said abrading surface has a width, said width being adapted to substantially match the width of the nucleus pulposus of a disc space, in which it is inserted.

13. The apparatus of claim 1, wherein said abrading surface is substantially planar.

14. The apparatus of claim 1, wherein said abrading surface is configured such that it is generally parallel to said surface contour formed in the vertebral body as said abrading element is moved by said drive mechanism.

15. The apparatus of claim 1, wherein said abrading element is detachable from said shaft.

16. The apparatus of claim 1, wherein said abrading element is fixedly connected to said shaft.

17. The apparatus of claim 1 further comprising a mechanism that couples said abrading element to said drive mechanism.

18. The apparatus of claim 1, wherein said drive mechanism is disposed at least in part in said handle.

19. The apparatus of claim 1, wherein said power source is disposed at least in part in said handle.

20. The apparatus of claim 1, wherein said abrading element is driven in a reciprocating, arcuate motion by said drive mechanism.

21. The apparatus of claim 1, wherein said abrading element includes a wheel having cutter teeth along its perimeter.

22. The apparatus of claim 1, wherein said drive mechanism is adapted to produce a rotary movement of said abrading element about an axis generally perpendicular to a longitudinal axis of said shaft and about a general plane of a vertebral end plate of at least one of the adjacent vertebral bodies.

23. The apparatus of claim 1, wherein said drive mechanism is adapted to produce one of an oscillating rotation and a vibratory motion of the abrading element.

24. The apparatus of claim 1, wherein said drive mechanism is adapted to produce an oscillating rotation of the abrading element, wherein said oscillating rotation is from 20° to 45° to either side of the longitudinal axis of said shaft.

25. The apparatus of claim 1, wherein said drive mechanism comprises a gas-driven turbine powered by a source of compressed gas.

26. The apparatus of claim 1, wherein said drive mechanism is operable to move said abrading element in at least two degrees of freedom.

27. The apparatus of claim 1, further comprising a suction mechanism for removing bits of debris created by said abrading surface of said abrading element.

28. The apparatus of claim 1, further comprising an irrigation channel configured through said shaft for delivering irrigation fluid to the surgical site.

29. The apparatus of claim 1, further comprising at least one stop member adapted to limit the depth of travel of said abrading element into the spine.

30. The apparatus of claim 1, further comprising an insert adapted to be sized and shaped to match the space formed in the spine by said abrading element.

* * * * *